United States Patent [19]

King et al.

[11] Patent Number: 5,120,659

[45] Date of Patent: Jun. 9, 1992

[54] DEUTERATED WATER TEST METHOD

[75] Inventors: William P. King, Washington; Ronald E. Thompson, North Huntingdon; both of Pa.

[73] Assignee: Mine Safety Appliances Company, Pittsburgh, Pa.

[21] Appl. No.: 371,518

[22] Filed: Jun. 26, 1989

[51] Int. Cl.⁵ ............................................ G01N 30/00
[52] U.S. Cl. ..................................... 436/39; 436/171; 436/178
[58] Field of Search ................. 436/39, 164, 171, 174, 436/178

[56] References Cited

U.S. PATENT DOCUMENTS 4,766,081  8/1988  Rückert .................................. 436/39

Primary Examiner—David L. Lacey
Assistant Examiner—Jeffrey R. Snay
Attorney, Agent, or Firm—Reed Smith Shaw & McClay

[57] ABSTRACT

A method for testing for the removal of tritiated water using deuterated water in which the infrared absorption spectra of deuterated water in an effluent stream passing through a tritiated water filtering media is measured.

4 Claims, 2 Drawing Sheets

DEUTERATED WATER TEST METHOD

FIELD OF THE INVENTION

The invention relates to a method for testing the efficiency of tritiated water removal using deuterated water and, in particular, a method for testing the efficiency of canisters or cartridges use in a respirator for filtering tritiated water from a gas.

BACKGROUND OF THE INVENTION

It is known to use an air purifying respirator to remove tritiated water vapor from the atmosphere. Presently, the exchange of higher hydrogen isotopes is achieved by using vermiculite beds. More recently respirator filters have been provided for the removal of tritiated water which include a filter material having a high surface area such as silica gel and activated carbon.

The efficacy of these filters is tested by passing tritiated water vapor through the filter until breakthrough is encountered. The gas passing through is measured for the tritiated water present. When the filter is unable to remove 95% of the tritiated water entering the filter, breakthrough is deemed to have occurred. Most specifications require that a 95% removal rate be maintained for at least 60 minutes.

However, because the methods available to test the efficiency and efficacy rely upon the use of tritiated water, manufacturers of respirators are required to send their devices to special laboratories equipped and licensed to handle tritiated water in order to determine whether or not their respirators meet specifications. This is both expensive and inconvenient.

Accordingly, it is an object of the present invention to provide a test method which does not involve the use of tritiated water but provides a reliable correlation with tritiated water tests. It is a further object of the invention to provide a test for testing the efficacy of tritiated water respirator canisters and cartridges.

SUMMARY OF THE INVENTION

The method of the present invention comprises passing a controlled amount of air through deuterated water to create a deuterated effluent stream which is directed through the filter to be tested. An infrared spectrophotometer is used to sample the effluent passing through the filter. When the effluent concentration exiting from the filter is 5% of the concentration of deuterated water entering the filter, breakthrough has occurred and the service life of the filter determined. This deuterium service and time correlates well to tritiated water to provide the service life for the tritiated water filters.

The time and expense to conduct the method of the present invention is less than prior art tests run with tritiated water. In addition, no radiation hazard is involved.

Other advantages of the invention will become apparent from a perusal of the following detailed description of a presently preferred embodiment taken in connection with the accompanying drawings.

PRESENTLY PREFERRED EMBODIMENT

Figure 1:
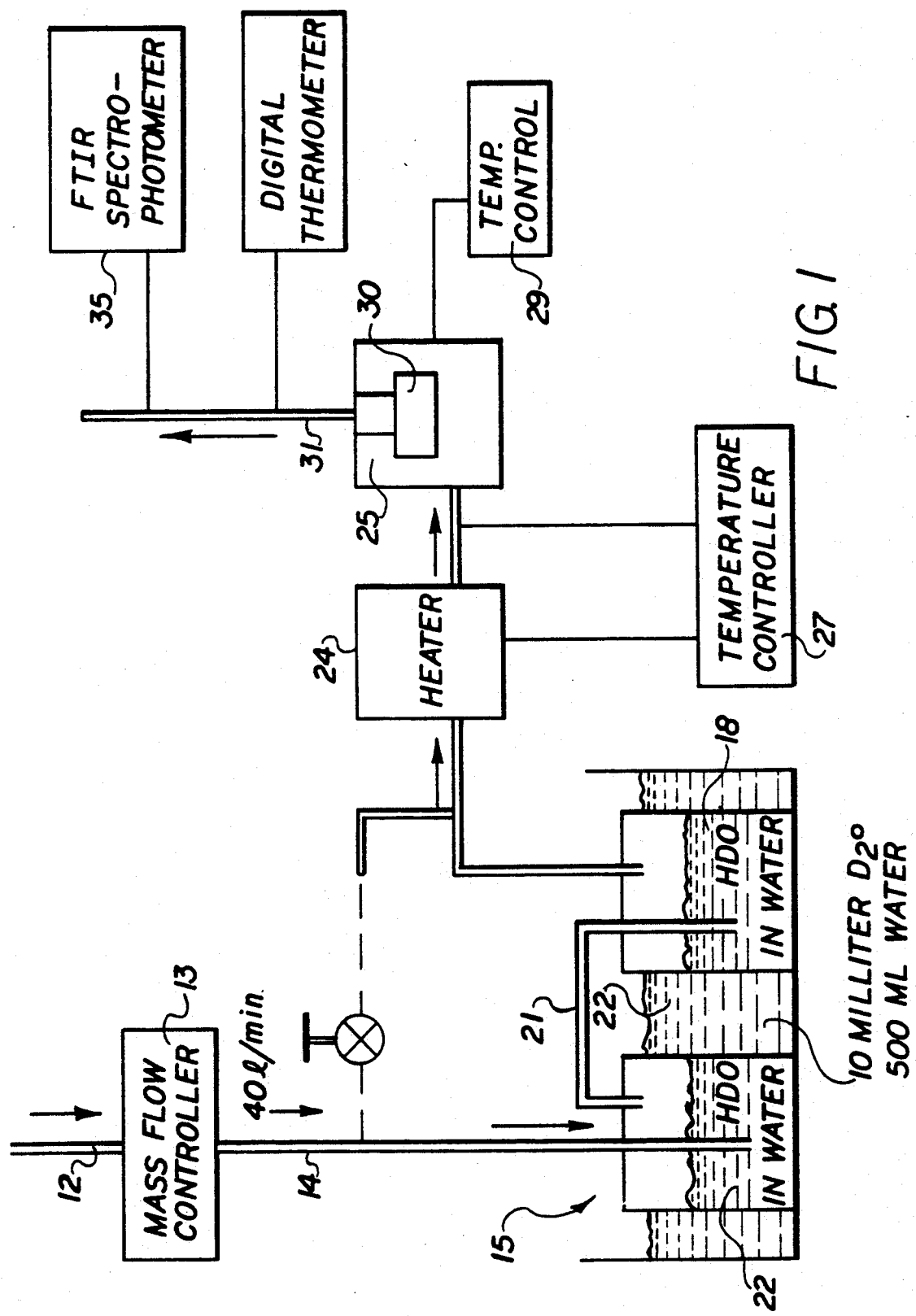
FIG. 1 is a schematic of the test equipment set up using the method of the present invention.
Figure 2:
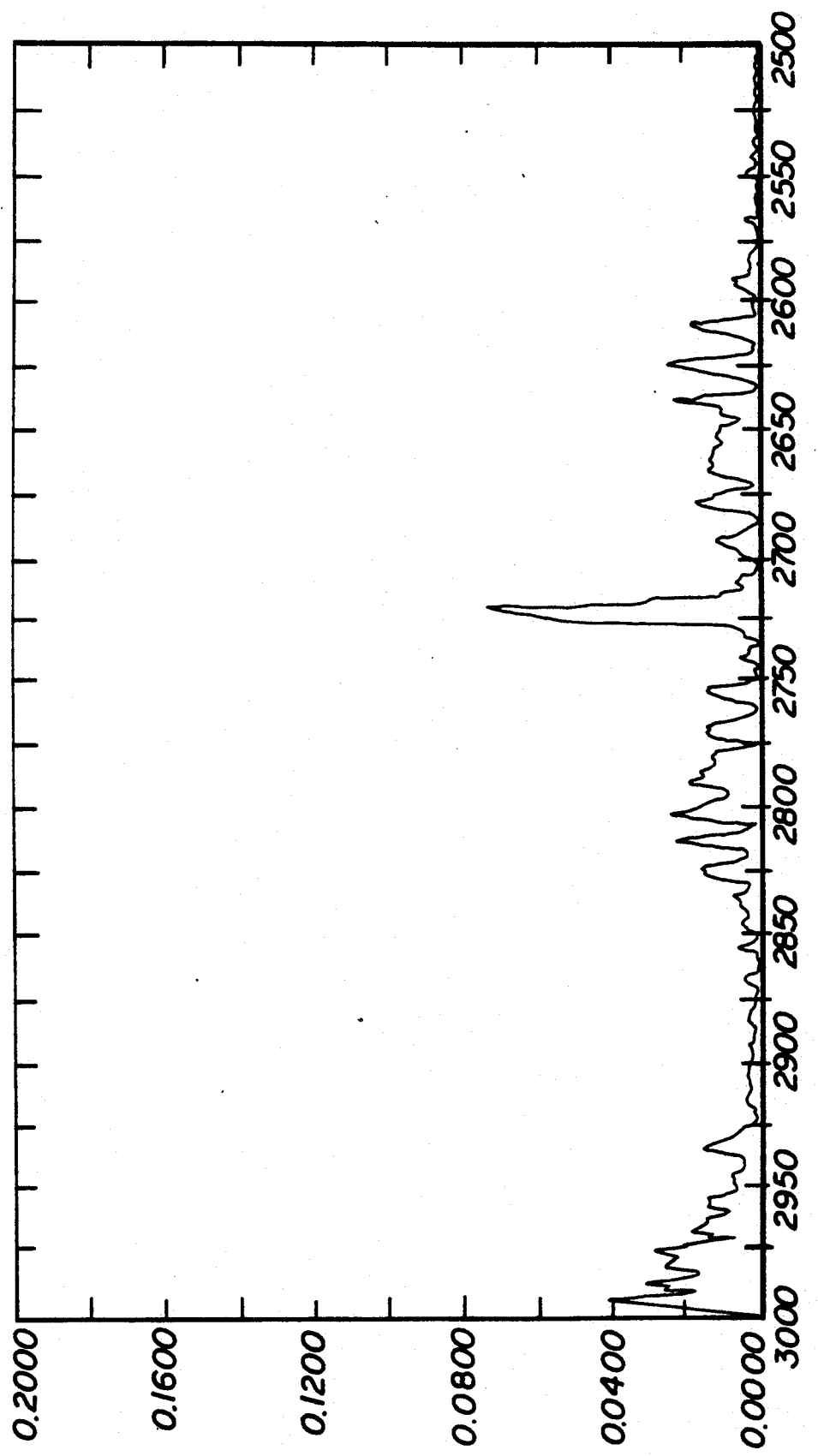
FIG. 2 is an IR spectrum showing deuterium IR absorption at 2722 $cm^{-1}$.

With reference to FIG. 1, a presently preferred embodiment of the test method of the invention is shown wherein air is directed through line 12 to mass flow controller 13. Mass flow controller regulates the quantity of air to preferably about 40 l/min. The regulated air is directed from regulator 13 by line 14 to test solution 15.

Test solution 15 generates 0.876 mg/l of deuterated water in air prepared by adding 10 ml of deuterium oxide to 500 ml of distilled water. As shown in FIG. 1, it is preferable to split the test solution into two bubblers 17 and 18 which are connected by means of tube 21. Bubblers 17 and 18 are maintained at 25° C. by means of water bath 22 or other temperature control means.

The effluent stream from bubbler 18 is directed via line 23 through heater 24 to test chamber 25. Heater 24 is controlled by controller 27 to maintain a temperature in effluent line 23 at about 25° C. Test chamber 25 is temperature controlled by controller 29 to a test temperature of 25° C.

Mounted within test chamber 25 is a canister or cartridge 30 containing the deuterated water filtration media. Effluent is exhausted from test chamber 25 through filter media 30 via line 31. Connected to line 31 is a thermometer 32 and an infrared spectrophotometer 35, preferably a fourier transform IR spectrophotometer (FTIR).

After the test stream effluent and chamber reach proper temperature, the test is commenced by starting the flow of air through the deuterated test solution. When this stream reaches equilibrium it is connected to chamber 25. At interval of from about 5 to 10 minutes, a spectrum is recorded and the absorbance measured at 2722 $cm^{-1}$ by the FTIR spectrophotometer 35. At the same time, the temperature of the effluent is recorded.

The end of service life is determined when the effluent stream of deuterated water reaches the concentration 0.044 mg/l. Service life is interpolated from the interval concentration levels.

Tests using the method of the present invention were run using tritium filters. These filters must remove 95% of the tritiated water entering a canister when exposed to $10^{-4}$ microcuries/cc for 60 minutes at a flow rate of 40 liters/minutes at 25° C. and 95% RH. Results of these tests are shown in Table I below in which the test method of the present invention is correlated with prior art tritiated water tests. The results shown in Table 1 differ from the service time to a specified maximum instantaneous penetration as described above. Instead, the removal efficiency over the test time was obtained by integration of instantaneous penetration results.

TABLE I

| | TEST CONDITIONS<br>40 Liters per minute<br>26 deg C.<br>min. 90% RH | | | |
|---|---|---|---|---|
| FILTER | TEST NUMBER | TEST TIME minutes | (Present Invention) % HDO REMOVED | (Prior Art) % HTO REMOVED |
| Canister with | 1 | 60 | 88.11 | 99.46 |
| 500 cc silica gel | 2 | 60 | 91.44 | 99.49 |
| (6 × 16) with | 3 | 60 | 94.42 | 99.60 |
| 5% moisture | 4 | 60 | | 99.58 |
| added 55 cc water | 5 | 60 | 96.92 | |
| to above | 6 | 60 | 98.47 | 99.84 |
| 120 cc water | 7 | 60 | >99.8 | 99.98 |
| to first | | 120 | >99.8 | 99.24 |
| | | 144 | 91.69 | 95.76 |
| (2) CARTRIDGES | 1 | 50 | 66.32 | |
| 105 cc carbon | | 60 | | 84.54 |
| (6 × 16) with | 2 | 40 | 74.14 | |
| 37% added water | | 60 | | 90.05 |
| | 3 | 40 | 74.32 | |
| CARTRIDGE | 1 | 60 | 93.74 | 98.07 |
| 150 cc carbon | | 72 | 85.32 | 81.92 |
| (12 × 20) with | 2 | 60 | 92.44 | 95.91 |
| 38% moisture | 3 | 60 | 81.00 | 95.04 |
| | 4 | 60 | | 95.64 |
| (2) CARTRIDGES | 1 | 60 | 98.6 | 98 average |
| 180 cc carbon | 2 | 60 | 98.3 | |
| (12 × 30) with | 3 | 60 | 96.8 | |
| 38% moisture | 4 | 60 | 97.1 | |

While a presently preferred embodiment of the invention has been shown and described in detail, it may be otherwise embodied within the scope of the appended claims.

What is claimed is:

1. A method for determining the efficacy of a filter material to remove tritiated water by evaluating the effective removal of deuterated water by the filter material, comprising:
   A. preparing an effluent stream of deuterated water;
   B. maintaining said effluent stream at a constant temperature and humidity;
   C. passing said effluent stream through said filter material to be tested for the efficacy to remove tritiated water; and
   D. measuring said effluent stream after passage through said filter material at selected time intervals by infrared absorption of deuterated water to determine the amount of deuterated water removed by said filter material to establish the efficacy of the filter material for removing deuterated water, the efficacy for removal of tritiated water being provided thereby since said efficacy for removal of tritiated water is substantially at least that of said efficacy for removal of deuterated water.

2. A method as set forth in claim 1, wherein said infrared absorption is measured by a fourier transform IR spectrophotometer.

3. A method as set forth in claim 1, wherein said intervals are about 5 minutes.

4. A method as set forth in claim 1, wherein said temperature is maintained between about 25° C. to 35° C. and the humidity is maintained between 90 and 95% RH.

* * * * *